(12) United States Patent
Gebauer (10) Patent No.: US 10,048,235 B2
(45) Date of Patent: *Aug. 14, 2018

(54) CHROMATOGRAPHY COLUMNS, SYSTEMS AND METHODS

(71) Applicant: GE Healthcare BioProcess R&D AB, Uppsala (SE)

(72) Inventor: Klaus Gebauer, Uppsala (SE)

(73) Assignee: GE Healthcare BioProcess R&D AB, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 15/379,447

(22) Filed: Dec. 14, 2016

(65) Prior Publication Data

US 2017/0097327 A1   Apr. 6, 2017

Related U.S. Application Data

(63) Continuation of application No. 14/252,874, filed on Apr. 15, 2014, now Pat. No. 9,527,009, which is a continuation of application No. 13/487,766, filed on Jun. 4, 2012, now Pat. No. 8,702,983, which is a continuation of application No. 11/879,126, filed on Jul. 16, 2007, now abandoned.

(51) Int. Cl.
| | |
|---|---|
| *G01N 30/60* | (2006.01) |
| *G01N 30/38* | (2006.01) |
| *B01D 15/22* | (2006.01) |
| *B01D 15/18* | (2006.01) |
| *B01D 15/26* | (2006.01) |

(52) U.S. Cl.
CPC ......... *G01N 30/6004* (2013.01); *B01D 15/18* (2013.01); *B01D 15/22* (2013.01); *G01N 30/606* (2013.01); *G01N 30/6017* (2013.01); *G01N 30/6021* (2013.01); *G01N 30/6052* (2013.01)

(58) Field of Classification Search
CPC ........ B01D 15/10; B01D 15/22; B01D 15/18; G01N 30/02; G01N 30/60; G01N 30/6004; G01N 30/6017; G01N 30/6021; G01N 30/603; G01N 30/6052; G01N 30/606
See application file for complete search history.

(56) References Cited

U.S. PATENT DOCUMENTS

| | | | |
|---|---|---|---|
| 3,640,813 | A | 2/1972 | Nerenberg |
| 4,537,217 | A | 8/1985 | Allen, Jr. |
| 5,213,683 | A | 5/1993 | Mann |
| 5,354,460 | A | 10/1994 | Kearney et al. |

(Continued)

FOREIGN PATENT DOCUMENTS

| | | |
|---|---|---|
| GB | 2 258 415 | 10/1993 |
| JP | 63-293465 | 11/1988 |

(Continued)

OTHER PUBLICATIONS

Gel Filtration Principles and Methods, Amersham Pharmacia Biotech, 8th Edition, 1998.

*Primary Examiner* — Katherine Zalasky
(74) *Attorney, Agent, or Firm* — Wood IP LLC (57) ABSTRACT

The present invention relates to axial flow chromatography columns, methods for separating one or more analytes in a liquid by the use of such columns, and systems employing such columns. The column comprises a first port and a second port, the first port and said second port being at essentially the same level or elevation above the level of the bed space on the chromatography column.

12 Claims, 7 Drawing Sheets

(56) References Cited

U.S. PATENT DOCUMENTS

| | | |
|---|---|---|
| 5,902,485 A | 5/1999 | Davis et al. |
| 6,117,317 A | 9/2000 | Dickson et al. |
| 6,123,849 A | 9/2000 | Purdom |
| 6,524,484 B2 | 2/2003 | Davis et al. |
| 9,527,009 B2 | 12/2016 | Gebauer |
| 2001/0013494 A1 | 8/2001 | Maiefski et al. |
| 2002/0035241 A1 | 3/2002 | Buchacher et al. |
| 2002/0125181 A1 | 9/2002 | Pichl et al. |
| 2002/0166816 A1 | 11/2002 | Allen et al. |
| 2007/0012626 A1 | 1/2007 | Andersson et al. |

FOREIGN PATENT DOCUMENTS

| | | |
|---|---|---|
| JP | 63293456 | 11/1988 |
| JP | 11-248695 | 9/1999 |
| WO | 1996010451 | 4/1996 |
| WO | 2001054786 | 8/2001 |
| WO | 2005009585 | 2/2005 |

CHROMATOGRAPHY COLUMNS, SYSTEMS AND METHODS

FIELD OF THE INVENTION

The present invention relates to axial chromatography columns and methods of separating one or more analytes present in a liquid from each other using such chromatography columns.

BACKGROUND OF THE INVENTION

Chromatography is a well-established and valuable technique for separating chemical and biological substances and is widely used in research and industry, finding many applications in compound preparation, purification and analysis. There are many different forms of chromatography, liquid chromatography being of particular importance in the pharmaceutical and biological industries for the preparation, purification and analysis of proteins, peptides and nucleic acids.

A typical liquid chromatography apparatus has an upright housing in which a bed of packing material, which is usually particulate in nature and consists of a porous medium, rests against a permeable retaining layer. A liquid mobile phase enters through an inlet, for example at the top of the column, usually through a porous, perforated filter, mesh or frit, moves through the bed of packing material and is removed via an outlet, typically through a second filter, mesh or frit.

Columns used in liquid chromatography typically comprise a tubular body enclosing the porous chromatography medium through which the carrier liquid or mobile phase flows, with separation of substances or analytes taking place between the mobile phase and solid phase of the porous medium. Typically, the porous medium is enclosed in the column as a packed bed, generally formed by consolidating a suspension of discrete particles, known as slurry that is pumped, poured or sucked into the column, usually from a central bore or nozzle located at one end of the column. The production of a stable, even bed is critical to the final separation process and optimum results are found using bores which are centrally positioned through the column end. Systems for producing such stable, even beds are known in the art and include, for example, compressing the bed by means of an end unit.

Following column packing and prior to use it is necessary too install the column by connecting it to a chromatography system, usually comprising a pump, detectors and inlet and outlet manifolds. When installing the column, it is essential to avoid any draining of the column from liquid as well as to avoid introduction of air into the column and the packed bed, respectively. Furthermore, it may be necessary to purge the system employing the column of any air upstream of the column. Typically, prior art columns and systems accomplish column installation and/or purging or venting by means of a valve (a "vent" or "purge" valve) at one end of the column, usually at its base.

In practice, the valve is used together with the column, which means that the column is connected and disconnected from the system upstream of the valve. For a disposable column, the introduction of such an additional valve is costly. By virtue of its position, it increases both the risk of siphoning of liquid from the column and also the likelihood of further air being introduced into the column. Furthermore, the position of the valve imposes constraints on locating the column within the laboratory and can cause problems in terms of user accessibility, since access to both the top and bottom of the column is required.

JP 63293456 (Sekisui Chemicals Co.) describes a column holder to support columns having been prepared with a stationary phase and being equipped with a discharge aperture at the base and a ventilation device at the top. The column holder is designed such that on the application of gravity or a centrifugal force, to facilitate chromatographic separation of materials on the stationary phase, any surplus fluid remaining above the stationary phase can be removed without allowing air to enter the stationary phase within the column. The discharge aperture is connected to a conduit which is branched at a position that is at the same or a higher level than the upper end of the stationary phase solution and has three open ends, a first at the connection point with the discharge aperture, a second at a position above the surface level of the solution and a third located below the level of the discharge aperture. The conduit is configured such that any surplus fluid can be removed from the column through the third open end where it is collected in an acceptor vessel.

Despite the high level of activity in the field of chromatography over many years there is still a need for a simple axial column that obviates the need for vent valve or complex column holder and reduces the risk of air entering the column and/or liquid siphoning from it. To date, no axial chromatography columns are available which meet this need and/or provide improved user accessibility.

DEFINITIONS

"Analyte" shall be defined as a substance, compound or chemical of natural synthetic origin, or a reaction product or derivative or metabolite thereof. For the avoidance of doubt, the term shall include biological molecules, such as proteins, peptides, amino acids and nucleic acids, and synthetic molecules such as drugs and/or pro-drugs.

"Distribution channel" refers to structures through which fluids are introduced to an enclosure bed space for a packed bed of chromatography medium from a cross-sectional zone.

A disposable column is characterized by a pre-treatment of the chromatography medium in order to reduce installation and qualification work otherwise required with non-disposable columns. As a minimum, the pre-treatment involves the formation of the bed of porous medium. Additional pre-treatment can be reduction of microbiological burden, sterilization, depyrogenation etc.

Disposable column may be used as single-use columns, which means that the user is not performing cleaning regimes that require qualification (e.g., testing, validation, etc) of the packed bed before repeated use.

One embodiment of a disposable column is a complete column that is delivered pre-packed with chromatography medium.

Another embodiment of a disposable column consists of a first device representing a frame or vessel designed to resist pressure and load exerted on one or multiple lateral surfaces of the packed bed during operation in order to provide dimensional stability for a packed bed, and a second device, representing a container, shell, cartridge, bag or the like containing the porous medium or bed that is attached to the first device for operation. With the latter embodiment, the porous medium is contained in the secondary container and can be replaced while the frame is re-usable. In this case, the degree of compression of the porous medium required for operation may be adjusted after inserting the contained medium into the frame (see, for example US2002/0166816, Allen & Dawson and WO2005/009585, Sigma-Aldrich Co.).

"Level" shall be defined as a horizontal plane or specified height.

SUMMARY OF THE INVENTION

The object of the invention is to provide a chromatography column which overcomes the drawbacks of the prior art systems. This is achieved by the chromatography column as defined in claim 1.

One advantage with such a chromatography column is that it reduces the risk of siphoning from the column.

Another advantage of the invention is that it is easy and cheap to produce, compared with existing columns that required an adjacent purge valve. This is especially important when using the column as a disposable column.

A further advantage of the chromatography is that it is easier to use than conventional columns because both the first port and second port which provide an inlet and an outlet for liquids such as mobile phase are at essentially the same level or elevation above the level of the bed space on one end of the column and thus provide improved user accessibility.

The simplicity of the design comprising few interconnected elements is advantageous in that it reduces the requirement for dynamic seals tightening and moving or rotating parts, as required for a (disposable) purge valve, hence decreasing the likelihood of leakage or contamination due to sanitary problems. These features are especially important for disposable columns comprising a reduction of microbiological burden during preparation (production) of the column, as well as to maintain those conditions during storage and shipping of the column.

Still a further advantage is that the chromatography column is scalable in that increasing or decreasing the column size leads to a predictable performance.

According to a first aspect of the invention, there is provided an axial flow chromatography column comprising:
a housing comprising a side wall;
opposed, axially spaced first and second end units separated by the side wall;
a first filter which is adjacent to the first end unit and a second filter which is adjacent to the second end unit wherein the filters together with the side wall define an enclosed bed space for containing a bed of particulate medium therein;
the first end unit comprising a first port which is in fluid communication with the enclosed bed space for adding a liquid to or removing a liquid from the bed space;
the second end unit comprising a second port which is in fluid communication with the enclosed bed space for adding a liquid to or removing a liquid from the bed space; and characterised in that the first port and the second port are at essentially the same level or elevation above the level of the bed space on the chromatography column.

In a second aspect, there is provided a method for separating one or more analytes in a liquid from each other, comprising applying the liquid containing the one or more analytes to an axial chromatography column as hereinbefore described, the column containing a bed of particulate medium therein, eluting the one or more analytes with a mobile phase, and collecting fractions of the mobile phase eluting from the column.

In a third aspect of the invention, there is provided a system for separating one or more analytes in a liquid from each other, the system comprising:
an inlet or inlet manifold in fluid communication with the liquid;
a pump;
a chromatography column as hereinbefore described; and an outlet or outlet manifold.

Embodiments of the invention are defined in the dependent claims.

DETAILED DESCRIPTION OF THE INVENTION

Figure 1:
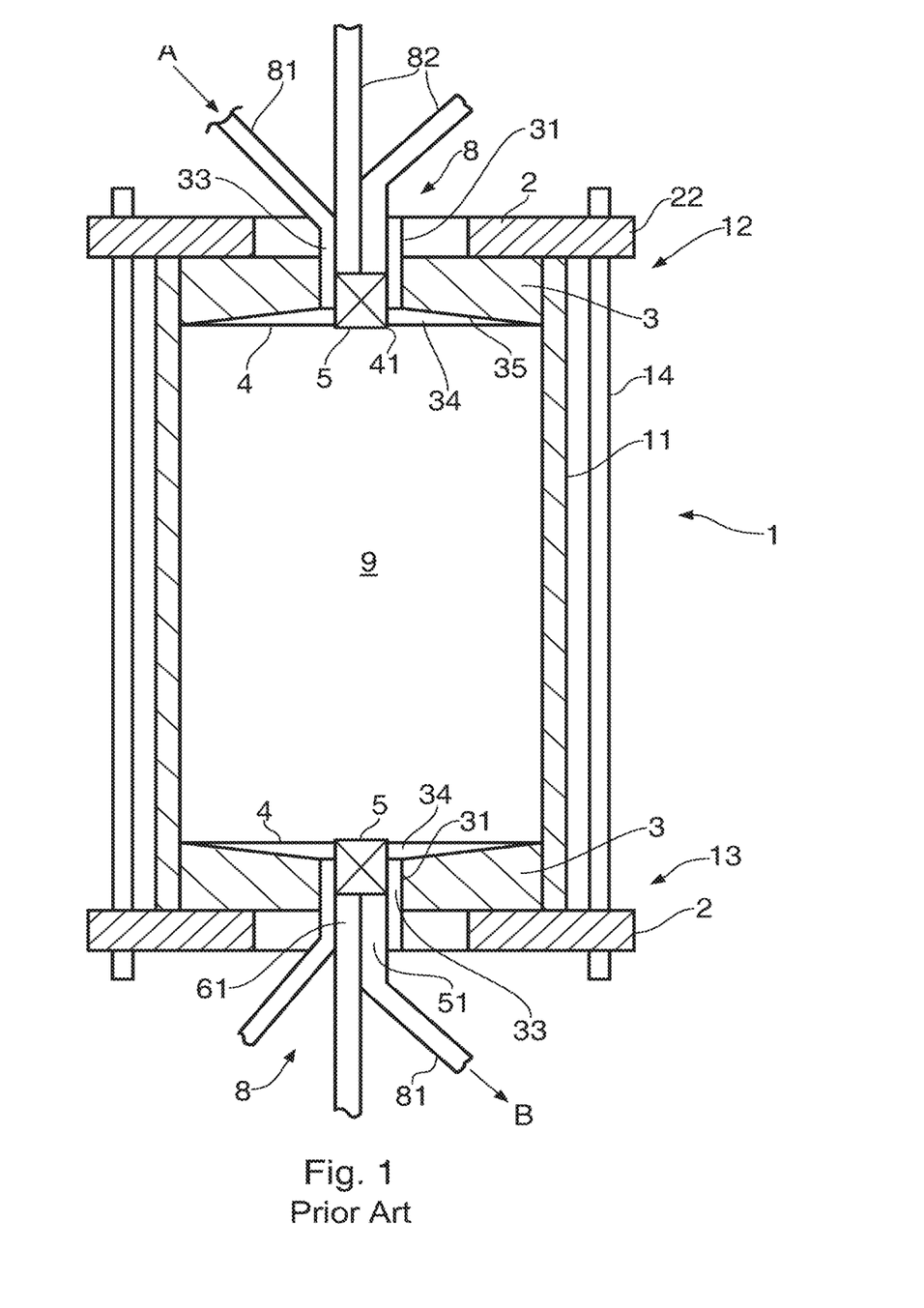
FIG. 1 is a schematic transverse sectional view of a chromatography column of the prior art showing the basic features thereof.

FIG. 1 shows schematically the general components of a chromatography column 1 as known from the prior art (for example, see U.S. Pat. No. 6,524,484). The column has a cylindrical fluid-impermeable side wall 11, e.g. of stainless steel or a high-strength/reinforced polymeric material which may be translucent. The open top and bottom ends of the side wall 11 are closed by top and bottom end assemblies or units 12, 13. Each end unit has a fluid-impermeable end plate 3 fitting sealingly to plug the opening of the cylindrical wall 11, and preferably made of stainless steel or high-strength engineering plastics material, e.g. polypropylene. The end plates are backed up by metal retaining plates 2 bearing against their outer surfaces and projecting radially beyond the side wall as retaining flanges 22 through which adjustable tension rods 14 are secured. These link the top and end assemblies 12, 13 and help the construction to withstand high fluid pressures.

Each end plate 3 has a central through-opening 31 for communication between the exterior of the column and the packing bed space 9 defined by the side wall 11 and end assemblies 12, 13. Access through the opening 31 is subdivided into separate conduits, connected externally through a connection manifold 8.

A filter layer 4, typically of filtered or woven plastics or steel, extends across the area of the bed space 9 at the inner surface of the end plate 3. The inner surface 35 of the end plate 3 is recessed behind the filter layer 4, e.g. conically as illustrated, and preferably with the use of support ribs (not indicated) supporting the filter layer 4 from behind, to define between them a distribution channel 34. One of the communication conduits, a mobile phase conduit 33, opens inwardly into this distribution channel 34, as well as outwardly to a mobile phase connector 81 of the manifold 8.

From the manifold 8, an access valve device 5 projects inwardly through the end plate opening 31 and sealingly through a central orifice 41 of the filter layer 4. The access valve 5, governs the communication of one or more conduits from the manifold 8 directly to the bed space 9, i.e. bypassing the filter layer 4. Indicated here are first and second valved conduits 51, 61 governed by the valve 5, and connected externally through connectors 82 of the manifold 8.

In a typical operation of the column, a packed bed of particulate stationary phase material fills the bed space 9 between the top and bottom filter layers 4. The valve devices 5 being closed, a mobile phase is fed in through mobile phase connector 81 (arrow "A"), passes through conduit 33 into the distribution channel 34 and through the filter layer 4 to elute down through the packed bed, effecting separation of its components or analytes. Liquid eluate passes thought the filter layer 4 of the bottom end assembly 13 and out through the mobile phase connect 81 thereof (arrow "B") for collection as appropriate. While this is an example of "downflow" chromatography, in that chromatographic separation is effected by the downward movement of the mobile phase through the column, the skilled person will understand that separation may alternatively be achieved by "upflow" chromatography, simply by pumping mobile phase upwards through the column and thus reversing the direction of flow. In this mode, mobile phase would enter the column at connector 81 (arrow "B"), move upwards through the stationary phase or particulate medium, and be collected from connector 81 (arrow "A") at the top of the column.

When installing the column, it is essential to avoid any draining of the column from liquid as well as to avoid introduction of air into the column and the packed bed, respectively. Furthermore, it may be necessary to purge the system employing the column of any air upstream of the column. This is achieved by means of a vent valve 5 which is located at the bottom of the column.

FIG. 1 and the above explanation are to illustrate general relationships of components and a typical mode of operation. The skilled person will understand, and it will also appear from the following description, that other specific constructions and modes of operation may be appropriate for different kinds of process.

Figure 2A:
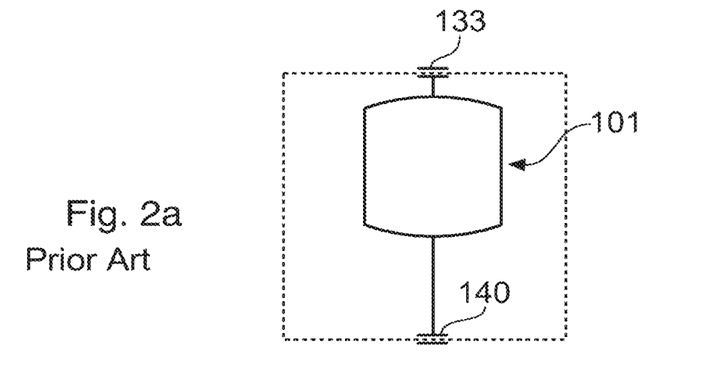
FIG. 2a, FIG. 2b and FIG. 2c are simplified schematic diagrams illustrating prior art (FIGS. 2a and 2b) columns and a column in accordance with the invention (FIG. 2c).
Figure 2B:
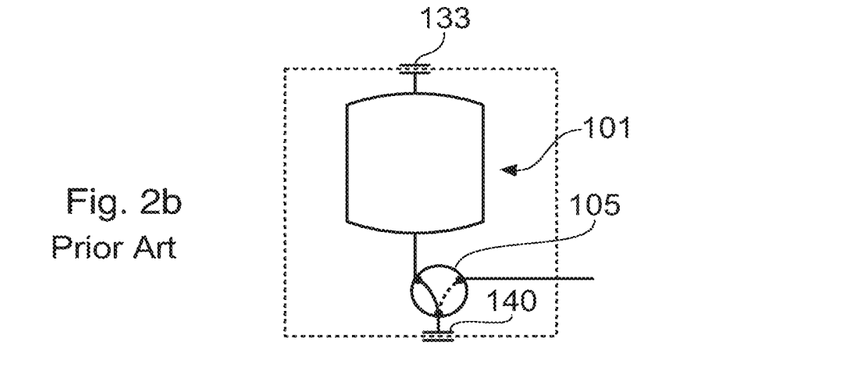

FIGS. 2a and 2b show simplified and schematic representations of the configuration of a prior art column. The column 101 has a first port 133 and a second port 140 for the introduction or collection of mobile phase. After installation of the column and prior to use, air needs to be removed from the column by means of venting/purging. This may be achieved by means of a vent valve 105 with a vent outlet which is either an integral part of the column 101 (as shown in FIG. 2b) or is connected to it at a point beyond the second port 140 (not shown in FIG. 2a).

Figure 2C:
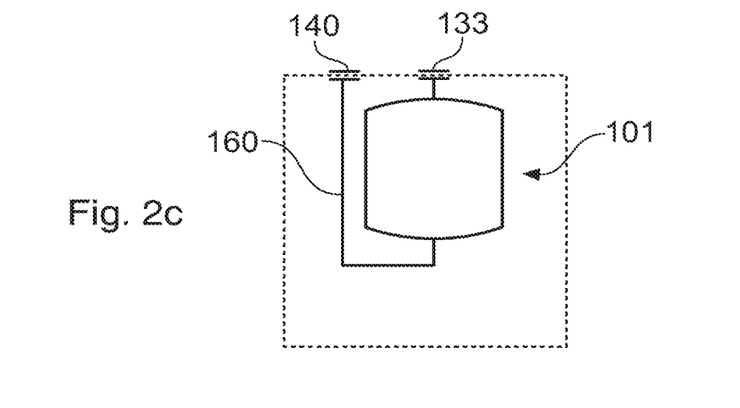

FIG. 2c is a simplified and schematic representation of a configuration of a column 101 in accordance with the invention. The first port 133, which is intended for the introduction or collection of mobile phase, is located at the top of the column 101 (as with columns of the prior art). The second port 140, which is in fluid communication with the bottom of the column, is at essentially the same level or elevation as the first port 133. This is achieved by means of a hollow member 160 which allows fluid such as air or mobile phase to flow between the bottom of the column 101 and second port 140. This configuration eliminates the need for a vent valve and reduces the risk of both siphoning from the column and introducing air into the column.

Figure 3:
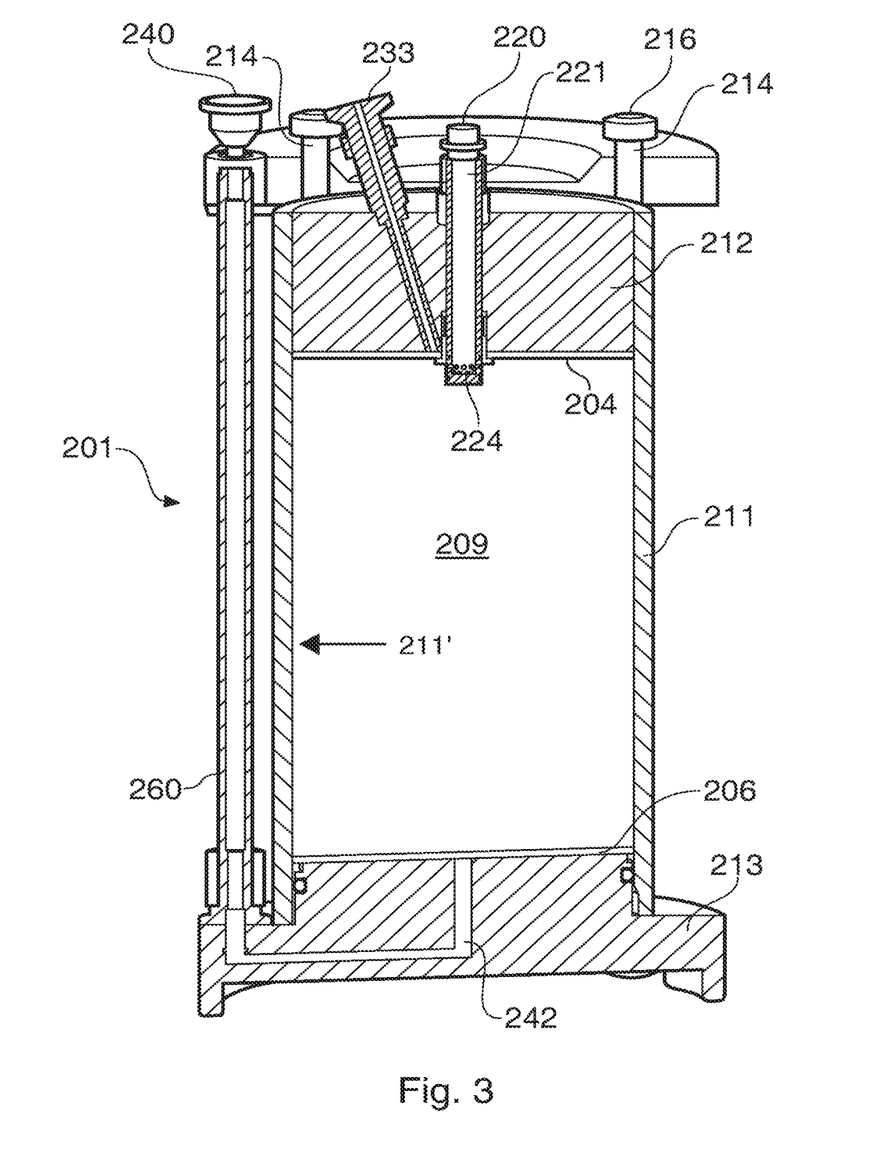
FIG. 3 is a transverse section of a column in accordance with the invention.

FIG. 3 shows a transverse sectional view of a column in accordance with the invention. The column 201 comprises a tubular housing 211, a first end unit 212 (partially shown) and a second end unit 213, secured together to form a fluid tight seal by means of tension rods 214 with heads 216. First filter 204 and second filter 206 are adjacent to the first end unit 212 and second end unit 213, respectively. These filters 204, 206, together with side wall 211, define a bed space 209 for containing a bed of particulate medium.

The housing 211 and end units 212, 213 are typically composed of stainless steel or a high-strength plastic material such as polypropylene. In a preferred embodiment, where the column is to be used for the separation of biologically active substances, the material is biologically inert such that it does not elicit an immune response in humans in accordance with United States Pharmacopia (USP) <88> class VI. Tension rods 214, with heads 216, secure the end units 212, 213 to the housing 211 to form a fluid-tight bed space 209 which is capable of withstanding high operating pressures.

Valve means 220 and first port 233 are shown in the figure. The second port 240 comprises a passageway 242 which extends through second end unit 213 to, and is in fluid communication with (via hollow member 260), bed space 209 from which liquid can be added or collected. As is evident from the figure, the second port 240 is at essentially the same level or elevation as the first port 233, thus facilitating the addition and collection of mobile phase to/from the column. This arrangement has further advantages in that it assists in the installation of the column, decreases the risk of syphoning and reduces the likelihood of introduction of air into the column.

The column can be packed with particulate medium in the form of a slurry through valve means 220, the valve means 220 comprising a central bore 221 and nozzle 224. A bed of packed particulate medium is obtained by conventional means well known in the art, for example by the movement of one of the end units to compress the bed. In FIG. 3 the nozzle 224 is shown in its retracted position but it will be understood that it can be moved to a position within the bed space 209 to facilitate filling of the column. A wide range of nozzles can be used which facilitate the distribution and even packing of slurry within the bed space. One alternative for achieving an open/closed functionality at the packing valve and nozzle respectively is to have a nozzle that is fixed in the bed space (and thus not retractable) and located adjacent to a moveable element or sleeve on the inside or outside of the nozzle that opens and/or closes the nozzle depending upon its position. Filters 204, 206 are each positioned on the interior face of the end units 212, 213 and act to define the bed space (together with side wall 211) and to prevent leakage of particulate medium from the bed space 209.

Mobile phase or liquid containing one or more analytes or substances for separation on the column is added via first port 233. The liquid then passes through the filter 204 into the bed space 209 that is packed with particulate medium (not shown). Chromatographic separation of analyte(s) which has been introduced onto the particulate medium in this manner is effected by introduction of, and elution by, mobile phase. The mobile phase will finally exit the column through second filter 206 and via passageway 242 to second port 240. The resulting fractions of mobile phase, which contain different analytes, can then be collected.

It will be understood by the skilled person that the column may be operated in either a "downflow" mode, as described above, or in an "upflow" where the direction of flow of the mobile phase is reversed such that it moves up the column. In upflow mode, mobile phase will enter the column via second port 240, move along passageway 242 and upwards through the bed of particulate medium in bed space 209, to exit the column for collection at first port 233.

In the embodiment shown, hollow member 260 is an integral part of the column. However, it will be understood that by means of connectors and appropriate tubing made from a suitable material (e.g. polypropylene, polyurethane, etc.) that the hollow member 260 need not be integral to the column.

The application and collection of mobile phase at the same elevation on a single end unit simplifies use, in terms of operator access and handling, reduces the risk of air accessing the system and decreases the space necessary to set up the column.

The embodiment shown in FIG. 3 comprises a valve means (220) for the introduction and/or removal of particulate medium from the column. It will be understood that such a valve is not an essential feature of the claimed invention as some columns (e.g. pre-packed, disposable columns) may not require the addition or removal of particulate medium to be performed by the end user or are prepared (packed) with a different technique not requiring the use of such a valve means.

Figure 4:
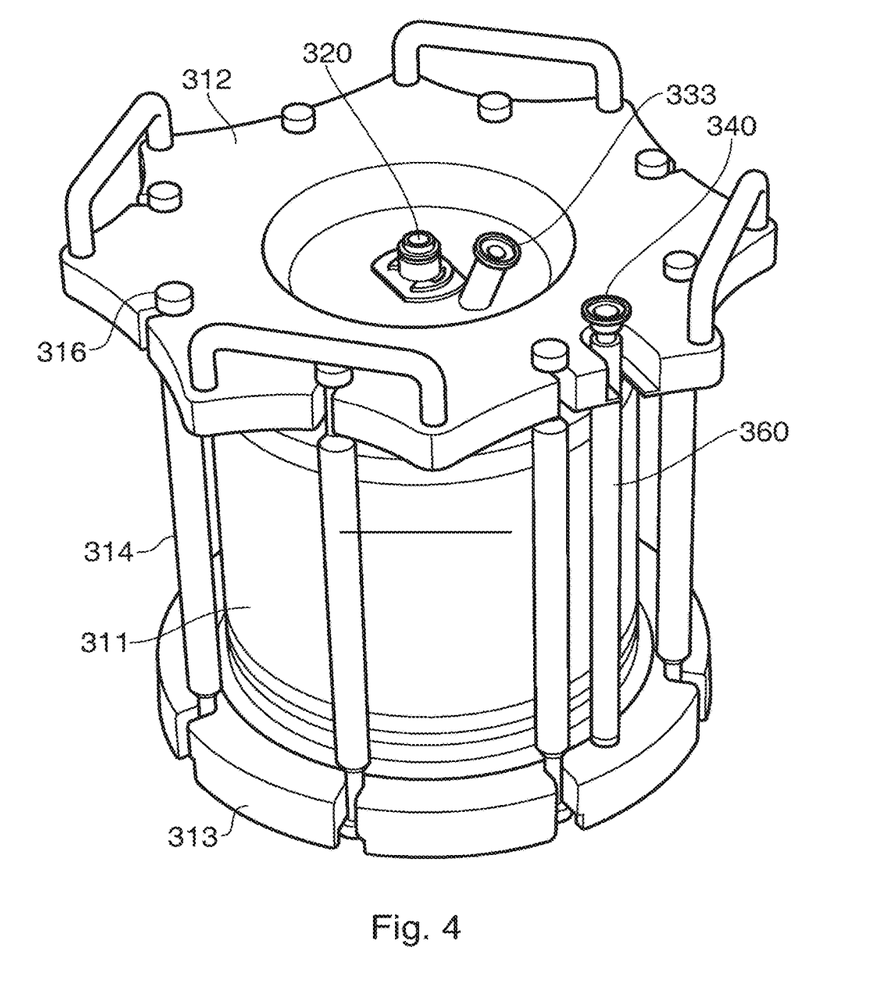
FIG. 4 is a three-dimensional schematic of a chromatography column according to the invention.

FIG. 4 presents a three dimensional schematic representation of the column of FIG. 3, from which the external features of the column are evident. The column comprises a first end unit 312, second end unit 313 and housing 311 which are secured together to form a fluid-tight seal by tension rods 314 and heads 316. Particulate medium in the form of a slurry can be introduced into the bed space (not shown) via valve means 320. First port 333 serves as a conduit for mobile phase or liquid containing analyte(s) to be separated on the particulate medium. Hollow member 360, which is in fluid communication with the bed space via an outlet at the base of the column (not shown), ends in second port 340 from which appropriate fractions of mobile phase eluted from the column may be collected. As can be seen, second port 340 is at essentially the same level or elevation as the first port 333 through which mobile phase can be introduced (or collected). This arrangement facilitates user operation and sample handling. In the embodiment shown in FIG. 4, the capacity of the column is approximately 10 liters; it will be understood that a wide range of column capacities is possible, typically ranging from 0.1 to 2000 liters. Preferred capacities when using the column as a disposable column are in the range of 0.5 to 50 liters.

Figure 5A:
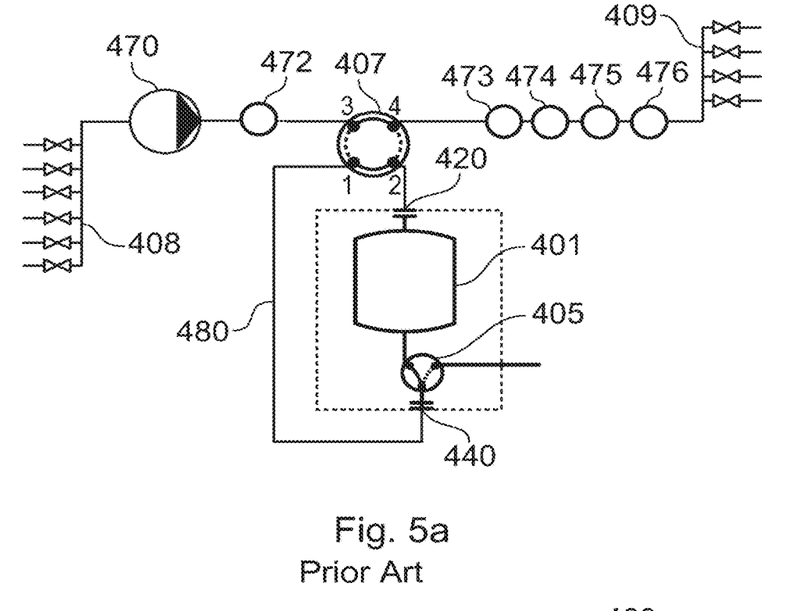
FIG. 5a is a schematic diagram of a system using a column known in the prior art.
Figure 5B:
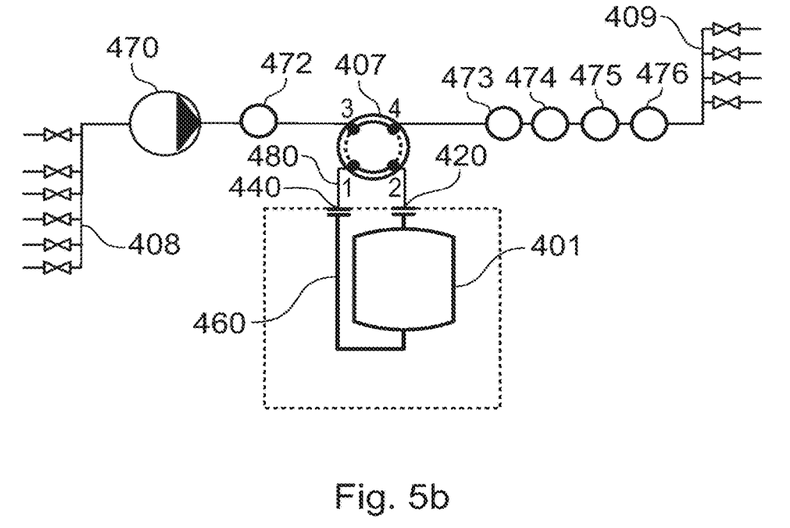
FIG. 5b is a schematic diagram of a system employing a column in accordance with the invention.

FIGS. 5*a* and 5*b* schematically compare a system incorporating a prior art column (FIG. 5*a*) having an integrated vent valve to a system using a column in accordance with the invention (FIG. 5*b*). The vent valve shown in FIG. 5*a* is a rotary valve type, but it will be understood that other valve principles (pinch valves, membrane valves, etc.) may also be employed to achieve the vent valve functionality.

Following installation of the prior art system (FIG. 5*a*), air must be removed from the system by priming it. The system comprises an inlet manifold 408, pump 470, sensors 472-476, column valve 407, outlet manifold 409 and column 401 (the dotted rectangle shown enclosing the column 401 and vent/purge valve 405 indicates that the column and the vent valve are used as a combined unit such that the vent valve is attached to the packed and primed column when installing the column in a chromatography system). As described above, the purpose of the vent valve is to protect the column from draining and/or the introduction of air when installing it in a system, or when removing/disconnecting the column from a system. The column valve 407 controls connection of the column 401 to the inlet 408 and/or outlet 409 manifolds and thus governs whether the column 401 is "offline" or "online". In FIGS. 5*a* and 5*b*, the column valve is of a rotary valve type, but it will be understood that other valve principles (e.g. pinch valves, membrane valves, etc) may also be employed to achieve the column valve functionality. Fluid connectivity with the column 401 and inlet 408/outlet 409 manifolds is controlled by means of several gateways within the valve 407 as indicated by positions 1-4 in the diagram). When valve 407 makes connection between positions 3 and 4 and positions 1 and 2, the column is bypassed. When the rotary valve is turned by 90 degrees, connection between positions 3 and 1 and in between positions 4 and 2 is made, which means that the column is inline or online and connected in upflow mode/flow direction. As explained above, other valve principles (e.g. pinch valves, membrane valves, etc) and a wide range of other valve configurations (upflow and/or downflow modes as well as connection of multiple columns) may be employed to achieve the column valve functionality.

Air is removed from the system by means of vent/purge valve 405 which allows priming of the system, in particular priming of conduit 480, and purging of any air within it.

The system shown in FIG. 5*a* is intended to be used in an upflow mode; thus liquid from inlet manifold 408 enters column 401 via conduit 480 at second port 440 and moves upwards through the packed bed (not shown) exiting at first port 420. Liquid (e.g. mobile phase or sample containing analytes to be separated on the column) is taken up from inlet manifold 408 and transferred to the column 401 under pressure by means of pump 470 via column valve 407. Sensors 472-476 can be used to measure environmental, physical and chemical conditions in the system (e.g. pressure, flow, conductivity, temperature, pH, UV absorbance, air etc). These sensors can be used to control the operation of the column, for example by regulating flow rates of mobile phase through the column. Liquid emerging from the column from first port 420 is transferred via column valve 407 to outlet manifold 409 for collection.

FIG. 5*b* exemplifies a system using a column in accordance with the invention. The component parts are the same as described above for FIG. 5*a* except that there is no vent/purge valve 405. In this configuration the level or elevation of the first port 420 and the second port 440 above the level of the bed space (not shown) in the column is essentially the same, the second port 440 being connected to the base of the column 401 by means of hollow member 460. While hollow member 460 is part of the column in accordance with the invention, the corresponding liquid conduit 480 in FIG. 5*a*, which shows the prior art configuration, is part of the chromatography system. The column according to the invention with its hollow member 460 is already purged of air and may be ready for use when installed in the system. Especially for disposable, ready-to-use columns, the invention avoids the need for a disposable purge valve delivered with each individual column, which significantly reduces cost.

Following installation, the system is purged upstream of the column valve 407 when column 401 is bypassed (i.e. the column is "offline"). When switching the column "inline", only a negligible volume of air will remain between the column valve 407 and conduit 480.

The system shown in FIG. 5b can then be used in essentially the same manner as described above for the prior art system. In upflow mode, liquid will be aspirated from manifold 408 by pump 470 and directed, via valve 407, into second port 440 of column 401. The liquid will then move up the column through a bed of particulate medium (not shown) to exit at first port 420 and be directed, by column valve 407, to outlet manifold 409 for collection. Sensors 472-476 can be used to monitor environmental, physical and chemical conditions within the system and thus to regulate its operation.

Figure 6:
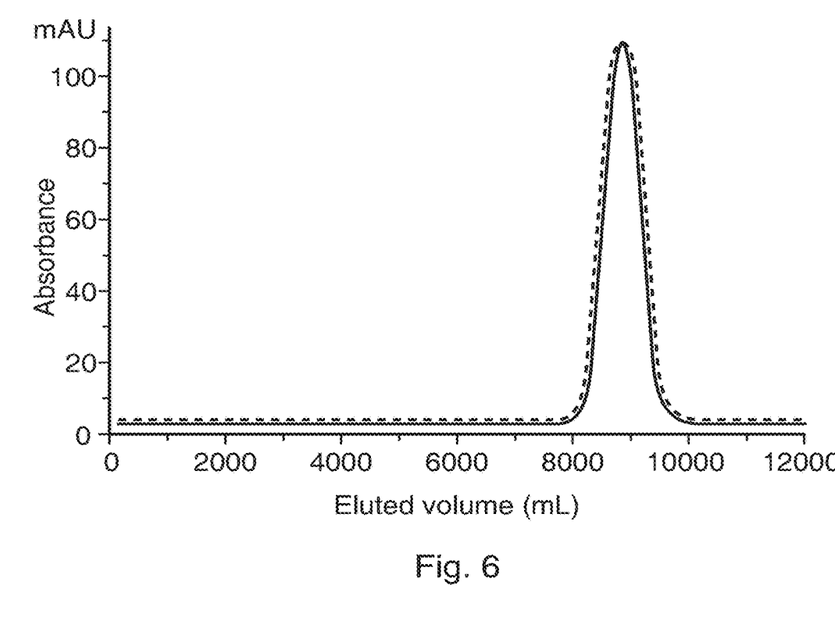
FIG. 6 is a chromatogram showing the chromatographic separation of acetone on a chromatography column according to the invention, both in upflow (dotted line) and downflow (solid line) mode.

FIG. 6 shows the chromatographic separation efficiency by example of a tracer pulse experiment achieved on a 10 liter column in accordance with the invention, operated in both downflow (solid line) and upflow (dotted line) mode. The column was packed with a bed of CAPTO™ Q anion exchange resin (GE Healthcare, Uppsala, Sweden) of 85 µm agarose particle diameter. The column had a volume of 10.81, a diameter of 263 mm and a bed height of 200 mm. Acetone (1% of packed bed volume) was used as a tracer substance and eluted from the column using water as mobile phase and the absorbance monitored at 280 nm. As can be seen from Table 1 below, excellent column efficiency was observed with the 85 µm agarose medium used, either in downflow (solid line) or upflow (dotted line) mode.

The data shown in Table 1 and FIG. 6 were obtained using a chromatography column in accordance with the invention which further comprises a transverse distribution channel and wherein the outlet of the first port and the transverse distribution channel have an asymmetric configuration. A chromatography column having such an arrangement is the subject of the Applicant's (GE Healthcare Bio-Sciences AB) co-pending patent application entitled "Axial Chromatography Columns and Methods" filed on the same day herewith as GB 0614316.8.

TABLE 1

| | Observed | Acceptance |
|---|---|---|
| Plates/meter (N/m) | 4430 | >3700 (for 85 µm) |
| Reduced plate height (h) | 2.5 | <3.0 |
| Peak asymmetry (Af) | 1.14 | 0.8-1.8 |

The data from Table 1 were derived from the chromatogram of FIG. 6 as described below.

Figure 7:
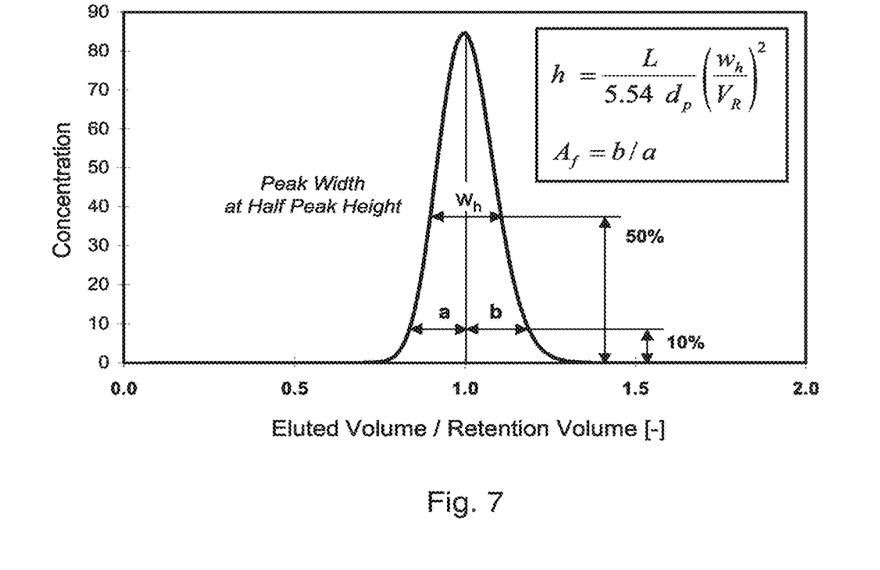
FIG. 7 describes a method for calculating the reduced plate height and asymmetry factor from an eluted peak.

As a measure for column efficiency, the reduced plate height is determined with help of the peak width $w_h$ at half the height of the eluted peak, as shown in FIG. 7. This procedure is an approximation valid for the gaussian-shaped. In practice, eluted peaks often deviate from this ideal gaussian shape and peak skewness is described qualitatively by so-called asymmetry factor $A_f$, where 'leading' in the RTD is indicated by $A_f<1$ and 'tailing' by $A_f>1$. Commonly applied acceptance criteria for the asymmetry factor are $0.8<A_f<1.5$-$1.8$, depending on the type of application.

$$h = \frac{HETP}{d_p} = \frac{L}{d_p}\frac{1}{5.54}\left(\frac{w_h}{V_R}\right)^2$$

$$A_f = b/a \text{ (see FIG. 7)}$$

As a rule of thumb, the characteristic dispersion of the medium typically gives a reduced plate height in the range h=1.5-2.0 at an optimized superficial velocity when considering the highly porous medium used for protein chromatography in biotechnological downstream processing. The ideal efficiency of the medium has to be compared to the experimentally determined efficiency of the chromatographic system, where an increase in the reduced plate height is a result of additional dispersion from peripherals, sample volume, bed heterogeneities and distribution system. In practice, a typical standard installation qualification of a chromatographic unit used in ion exchange separations of proteins is an experimentally determined reduced plate height of $h_{Unit,\ Apparent}<3.0$.

$A_f$ asymmetry factor
$d_p$ particle diameter
h reduced plate height
HETP height equivalent of a theoretical plate
L bed height, packed bed
$u_s$ superficial velocity in packed bed
$V_R$ retention volume
$w_h$ peak width at 50% of max. peak height It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. An axial flow chromatography column comprising:
   a housing comprising a side wall;
   axially spaced first and second end units positioned opposed to each other are separated by said side wall;
   a first filter which is adjacent to said first end unit and a second filter which is adjacent to said second end unit wherein said first and second filters together with the side wall define an enclosed bed space for containing a bed of particulate medium therein;
   the first end unit including a first port which is in fluid communication with said enclosed bed space for adding a liquid to or removing a liquid from the enclosed bed space;
   a second port being attached directly to the first end unit and being in fluid communication with the enclosed bed space via a passageway within the second end unit connecting to a hollow member extending from the second port at the first end unit adjacent to said sidewall; and
   wherein said second port is disposed at or above the same level or elevation of the first port and both the first port and the second port are above the level of the enclosed bed space of said chromatography column.

2. The chromatography column of claim 1, wherein said hollow member is an integral part of the column.

3. The chromatography column of claim 1, wherein said passageway extends from the enclosed bed space through a lateral wall of the second end unit.

4. The chromatography column of claim 1, wherein the first end unit additionally includes a valve means which is in fluid communication with the enclosed bed space, the valve means includes a longitudinal member extending through said first filler and having a passageway therein, the valve being operably openable and closable to allow filling of the enclosed bed space with a particulate medium through said passageway.

5. The chromatography column of claim 4, wherein said longitudinal member of said valve means comprises a nozzle.

6. The chromatography column of claim 5, wherein said nozzle is fixed within the enclosed bed space or retractable to a position outwith the enclosed bed space.

7. The chromatography column of claim 1, wherein said valve means does not allow emptying of the enclosed bed space of particulate medium.

8. The chromatography column of claim 7, wherein said chromatography column is pre-packed with particulate medium.

9. The chromatography column of claim 7, wherein said chromatography column is a disposable column.

10. A method for separating one or more analytes in a liquid from each other, comprising:
- applying said liquid containing said one or more analytes to a chromatography column of claim 1, said chromatography column containing a bed of particulate medium therein;
- eluting said one or more analytes with a mobile phase; and
- collecting fractions of said mobile phase eluting from the chromatography column.

11. A system for separating one or more analytes in a liquid from each other, said system comprising:
- an inlet or inlet manifold in fluid communication with said liquid;
- a pump;
- a chromatography column of claim 1; and
- an outlet or outlet manifold.

12. The system of claim 11, further comprising a valve operably openable and closable to allow the addition of liquid to, or the removal of liquid from, the enclosed bed space.

* * * * *